(12) United States Patent
Schmidt et al.

(10) Patent No.: US 11,538,152 B2
(45) Date of Patent: Dec. 27, 2022

(54) METHOD FOR PROVIDING AN AGGREGATE ALGORITHM FOR PROCESSING MEDICAL DATA AND METHOD FOR PROCESSING MEDICAL DATA

(71) Applicant: Siemens Healthcare GmbH, Erlangen (DE)

(72) Inventors: Christian Schmidt, Nuremberg (DE); Max Schoebinger, Hirschaid (DE); Michael Wels, Bamberg (DE)

(73) Assignee: Siemens Healthcare GmbH, Erlangen (DE)

( * ) Notice: Subject to any disclaimer, the term of this patent is extended or adjusted under 35 U.S.C. 154(b) by 149 days.

(21) Appl. No.: 16/898,743

(22) Filed: Jun. 11, 2020

(65) Prior Publication Data

US 2020/0402230 A1 Dec. 24, 2020

(30) Foreign Application Priority Data

Jun. 21, 2019 (EP) ..................................... 19181607

(51) Int. Cl.
*G06T 7/00* (2017.01)
*G06T 7/10* (2017.01)
(Continued)

(52) U.S. Cl.
CPC .......... *G06T 7/0012* (2013.01); *G06K 9/6256* (2013.01); *G06K 9/6262* (2013.01);
(Continued)

(58) Field of Classification Search
CPC ..................... G06T 7/0012; G06T 7/10; G06T 2207/20081; G06H 30/00; G06N 20/00;
(Continued)

(56) References Cited

U.S. PATENT DOCUMENTS 11,139,961 B2 * 10/2021 Baracaldo Angel ........................ G06N 3/0454
2014/0219548 A1 * 8/2014 Wels ...................... A61B 6/025
382/154

(Continued)

FOREIGN PATENT DOCUMENTS

EP 3101599 A2 12/2016

OTHER PUBLICATIONS

Federated Machine Learning: Concept and Applications, Yang et al., ACM Transactions on Intelligent Systems and Technology, vol. 10, No. 2, Article 12. Publication date: Jan. 2019 (Year: 2019).*
(Continued)

*Primary Examiner* — Vikkram Bali
(74) *Attorney, Agent, or Firm* — Harness, Dickey & Pierce, P.L.C.

(57) ABSTRACT

A method is for providing an aggregate algorithm for processing medical data. In an embodiment, a multitude of local algorithms are trained by machine learning. The training of each respective local algorithm is performed on a respective local system using respective local training data. A respective algorithm dataset concerning the respective local algorithm is transferred to an aggregating system that generates the aggregate algorithm based on the algorithm datasets.

21 Claims, 2 Drawing Sheets

(51) Int. Cl.
   *G16H 30/00* (2018.01)
   *G06N 20/00* (2019.01)
   *G06K 9/62* (2022.01)

(52) U.S. Cl.
   CPC ............... *G06N 20/00* (2019.01); *G06T 7/10* (2017.01); *G16H 30/00* (2018.01); *G06T 2207/20081* (2013.01)

(58) Field of Classification Search
   CPC ... G06K 9/6256; G06K 9/6262; G06K 9/6271
   See application file for complete search history.

(56) References Cited

U.S. PATENT DOCUMENTS

2016/0358099 A1   12/2016  Sturlaugson et al.
2018/0018590 A1*  1/2018  Szeto .................. G06F 21/6254

OTHER PUBLICATIONS

European Search Report for European U.S. Appl. No. 19/181,607 dated Nov. 5, 2019.

* cited by examiner

METHOD FOR PROVIDING AN AGGREGATE ALGORITHM FOR PROCESSING MEDICAL DATA AND METHOD FOR PROCESSING MEDICAL DATA

PRIORITY STATEMENT

The present application hereby claims priority under 35 U.S.C. § 119 to European patent application number EP 19181607.3 filed Jun. 21, 2019, the entire contents of which are hereby incorporated herein by reference.

FIELD

Embodiments of the invention generally relate to a method for providing an aggregate algorithm for processing medical data, especially medical image data, and a method for processing medical data. Additionally, embodiments of the invention concern a system, a computer program and a computer-readable storage medium.

BACKGROUND

In recent years there has been an upswing in interest and research in the areas of artificial intelligence and machine learning. Technologies such as deep learning enabled a significant quality leap in fully automated algorithms for segmenting and classifying image data, allowing such algorithms to be used in medical data processing and especially the processing of medical image data. The most common approach used in machine learning is supervised learning that requires training data to train an algorithm. Typically, it is necessary to manually identify at least the features that need to be detected and/or qualified in the training data and optionally also certain features that are evaluated by the algorithm to reduce the complexity of the data and make patterns more visible for the learning process.

In deep learning the algorithm itself learns the high-level features from annotated data in an incremental manner. Hence the performance of the algorithm depends to a large extend on the amount of data and the quality of annotations being used to train the algorithm. This is especially true since a multitude of variables need to be taken into account, e.g. an anatomical and/or pathological variability between the patients and/or a variability of the used imaging procedures or other acquisition protocols.

It is therefore a major challenge for the manufacturers of medical devices and other suppliers of such trained algorithms to assemble a sufficiently large and sufficiently well annotated set of training data. It can e.g. be necessary to use more than 10.000 or more than 100.000 sets of training data. In medical imaging there are also major privacy concerns, since medical image data and other medical data concerns highly private information. Therefore, an extensive anonymisation protocol needs to be implemented and it can be an elaborate process to gain access to large datasets that could e.g. be provided by hospitals. Once a sufficiently large dataset is acquired it is also typically necessary to manually annotate this extensive dataset by in-house experts or contractors. This might also require an acquisition of relevant knowledge.

Further the data processing can include the transfer of data across national borders and therefore additional requirements concerning data protection, especially considering a multitude of country-specific regulations. An inclusion of third parties for data processing typically requires the agreement of the original patients. These additional limitations limit the possibilities of outsourcing and data sharing.

The overall result of the issues mentioned above tends to lead to slow update and feedback cycles for products using machine learning.

From the document US 2014/0219548 A1 it is known to use local machine learning on an end user system. While this approach allows for an immediate improvement of the algorithm depending on user feedback, the algorithm can only profit from the local training. Since the pool of locally available training data is typically rather small, only a slow improvement of the algorithm is possible. The local algorithm can also not profit from any training performed in other locations. For processing medical data it is also desirable to perform a validation of the trained algorithm before the algorithm is released and used, to ensure that there is no unexpected behaviour of the algorithm. This is typically performed by the provider of the algorithm, e.g. the manufacturer of the medical device used. There is no simple approach for integrating such a validation in the approach used for local learning discussed in the mentioned document.

A different approach to using local data for training an algorithm is discussed in the document US 2018/0018590 A1. This document suggests to generate proxy data on the local system that has a similar distribution of data as the actual data. This proxy data is then aggregated from multiple systems and used to train the algorithm. While this approach improves the privacy compared to a direct redistribution of the local private data, transmitting information about the distribution of certain private data from e.g. a local hospital might already be problematic, especially if some of the data concerns a rare condition. Therefore, additional steps would be necessary to ensure that no privacy relevant data is accidently shared by the method proposed in this document. The creation of artificial data distributions that are similar to the true data distribution can also be problematic since algorithms used in machine learning, e.g. neural networks, can be highly nonlinear systems. A distribution that looks similar can therefore cause vast differences in the resulting trained algorithm. While the document suggests to check for this fact by using a local training using the real data and the proxy data and comparing the trained algorithms, it cannot be guaranteed, that this similarity of behaviour still holds true when multiple proxy datasets are merged and used for training.

SUMMARY

At least one embodiment of the present invention provides a method for providing an aggregate algorithm for processing medical data and therefore also to provide a method for processing medical data that allows for the use of local training data while at the same time ensuring that privacy concerns about this data are respected.

At least one embodiment of the present invention is directed to a method for providing an aggregate algorithm for processing medical data, especially medical image data, wherein a multitude of local algorithms is trained by machine learning, wherein the training of each respective local algorithm is performed on a respective local system using respective local training data, wherein a respective algorithm dataset concerning the respective local algorithm is transferred to an aggregating system that generates the aggregate algorithm based on the algorithm datasets (e.g. a plurality algorithm datasets of respective local algorithms). The method can be computer-implemented on an aggregating system which can comprise appropriate interfaces for receiving input data (e.g. the respective local algorithm) and providing output data (e.g. the aggregate algorithm)

In at least one embodiment, the training of each respective local algorithm itself can be provided as a (computer-implemented) method. It can comprise:

receiving input training data, e.g. with a first training interface), receiving output training data, e.g. with a second training interface), wherein the output training data is related to the input training data, training a function based on the input training data and the output training data, e.g. with a training computation unit, and providing the trained function, e.g. with a third training interface.

At least one embodiment of the invention also concerns an aggregate algorithm provided by the previously discussed method and a computer-readable storage medium containing information representing this algorithm. Information representing this algorithm can be a program or an instruction set implementing the trained algorithm or it can provide parameters determined during the training that parametrized a given algorithm comprising multiple free parameters, e.g. a neural network.

At least one embodiment of the invention also concerns a method for processing medical data, especially medical image data, wherein the medical image data is processed by an aggregate algorithm that is generated by the inventive method discussed above to generate output data. The previously mentioned training is not a necessary part of the method for processing medical data, but the usage of the trained aggregate algorithm is part of this method.

Thus, in the most general terms, this embodiment of the invention provides a method for providing output data, namely processed medical image data. It can be a computer-implemented method and it e.g. comprises:

receiving input data, e.g. with a further first interface), applying a trained function/function trained by a machine learning algorithm (i.e. the aggregate algorithm) to the input data, e.g. with a computation unit, wherein the output data is generated, and providing the output data, e.g. with a further second interface.

At least one embodiment of the invention also concerns a system comprising at least one processing unit configured to perform the function of the aggregating system in at least one embodiment of the inventive method for providing an aggregate algorithm and/or to perform at least one embodiment of the method for processing medical data. If the processing unit is configured to perform a method for processing medical data it can e.g. be integrated in a medical imaging device or be a work station used to evaluate the data from the medical imaging device. It is however also possible to perform this function e.g. by a server, a network comprising multiple servers or a cloud solution. The aggregating system will in many use cases require a relatively large amount of resources and can therefore e.g. be implemented on a server or a network of multiple servers or as a cloud solution. In some applications it can however also be advantageous to implement this functionality on a workstation or within a medical imaging system.

When the system comprises a processing unit configured to perform the function of the aggregating system it can additionally comprise multiple further processing units that are configured to perform the functions of the local systems in the method for providing an aggregate algorithm and/or to perform the method for processing medical data. In this case the system can especially be configured to implement the complete method for providing an aggregate algorithm. It is especially possible that the local systems are also used to process medical data as discussed above.

At least one embodiment of the invention further relates to a computer program that can be directly loaded into a memory unit of a processing unit, the computer program comprising instructions for performing the function of the aggregating system in the method for providing an aggregate algorithm and/or for performing at least one embodiment of the method for processing medical data when the program is executed on a processing unit.

At least one embodiment of the invention further relates to a computer-readable storage medium containing electronically readable instructions comprising the computer program.

At least one embodiment of the invention further relates to a method for providing an aggregate algorithm for processing medical data, the method comprising:

training a multitude of local algorithms by machine learning, the training of each respective local algorithm, of the local algorithms, is performed on a respective local system using respective local training data; and generating the aggregate algorithm based on the algorithm datasets by transferring each respective algorithm dataset, concerning the respective local algorithm, to an aggregating system.

At least one embodiment of the invention further relates to a system comprising:

at least one processor configured to train a multitude of local algorithms by machine learning, the training of each respective local algorithm, of the local algorithms, is performed on a respective local system using respective local training data; and generate an aggregate algorithm based on the algorithm datasets by transferring each respective algorithm dataset, concerning the respective local algorithm, to an aggregating system.

At least one embodiment of the invention further relates to a non-transitory computer program product storing computer program, directly loadable into a memory of a processor, the computer program including instructions for performing the method of claim 1 when the program is executed by the processor.

At least one embodiment of the invention further relates to a non-transitory computer-readable storage medium storing electronically readable instructions for performing the method of claim 1 when the program is executed by a processor.

BRIEF DESCRIPTION OF THE DRAWINGS

Other objects and features of the present invention will become apparent from the following detailed description considered in conjunction with the accompanying drawings. The drawings, however, are only examples and schematic solely for the purpose of illustration and do not limit the invention. The drawings show.

DETAILED DESCRIPTION OF THE EXAMPLE EMBODIMENTS

Figure 1:
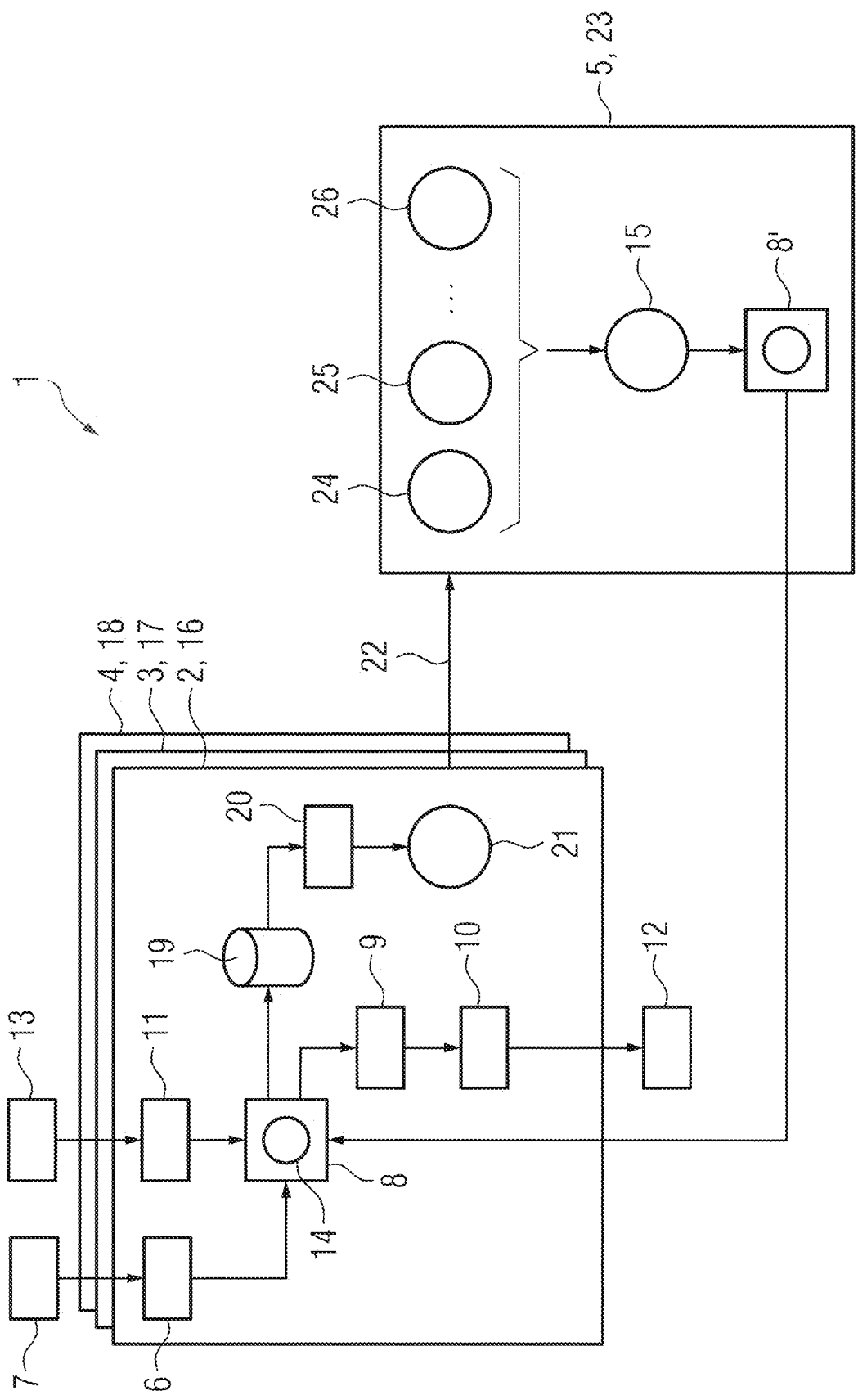
FIG. 1 an example embodiment of a system configured to perform example embodiments of the inventive method for providing an aggregate algorithm and for processing medical data according to the present invention, FIG. 2 a flow chart of an example embodiment of the method for providing an aggregate algorithm according to the present invention, and FIG. 3 the use of initial training data in an example embodiment of the method for providing an aggregate algorithm according to the present invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central At least one processor (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central At least one processor (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer at least one processors into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the present invention is directed to a method for providing an aggregate algorithm for processing medical data, especially medical image data, wherein a multitude of local algorithms is trained by machine learning, wherein the training of each respective local algorithm is performed on a respective local system using respective local training data, wherein a respective algorithm dataset concerning the respective local algorithm is transferred to an aggregating system that generates the aggregate algorithm based on the algorithm datasets (e.g. a plurality algorithm datasets of respective local algorithms). The method can be computer-implemented on an aggregating system which can comprise appropriate interfaces for receiving input data (e.g. the respective local algorithm) and providing output data (e.g. the aggregate algorithm)

In at least one embodiment, the training of each respective local algorithm itself can be provided as a (computer-implemented) method. It can comprise:

receiving input training data, e.g. with a first training interface), receiving output training data, e.g. with a second training interface), wherein the output training data is related to the input training data, training a function based on the input training data and the output training data, e.g. with a training computation unit, and providing the trained function, e.g. with a third training interface.

In this approach it is possible to only use the local training data locally to train the respective local algorithm. Therefore, the local training data that typically comprises private information or any information that allows drawing conclusions about such private information does not need to be transferred to the aggregating system. In machine learning approaches it is typically not possible to reconstruct the training data from the trained algorithm. Therefore, the suggested method implicitly implements protection of the private data that might be part of the local training data. The suggested method therefore allows for using local training data while automatically respecting any privacy concerns regarding this data. Preferably none of the local training data is transferred to the aggregating system, e.g. from a local hospital to the manufacturer of a medical device or some other provider of algorithms for the processing of medical data. The aggregate algorithm can be independent of the local training data except for the indirect dependence via the algorithm dataset.

The algorithm dataset can describe the complete local algorithm or parameters that are used to parametrize a given basic algorithm. Such parameters can e.g. be the input weights of individual nodes of a neuronal network.

The output of the local algorithm and/or the aggregate algorithm can e.g. be a classification of a depicted feature, a segmentation of an image or information concerning this segmentation, a probability of a certain medical condition etc. The local algorithm and the aggregate algorithm can provide the same type of output data. It is however also possible that the aggregate algorithm is a more complex algorithm that comprises at least one sub-algorithm generated in dependence of the local algorithms. It might e.g. be possible to only use the local training data to locally train the local algorithm for edge detection and use the respective algorithm datasets describing these local algorithms to generate an aggregate algorithm that performs a more complex segmentation task. It is also possible to use the local machine learning to teach a multitude of local algorithms that are than used to provide different sub-algorithms of the aggregate algorithm.

The local algorithm can be a neural network, especially a deep neuronal network, a decision tree, e.g. a random tree, or any other kind of algorithm usable in machine learning. Multitudes of such algorithms are known in the prior art and will therefore not be discussed in detail. The local algorithm can be completely described by the algorithm dataset or by the algorithm dataset and given prior information that can e.g. describe the given basic algorithm. In the second case the algorithm dataset can describe the parameters used to parametrize the given basic algorithm.

In general, a trained function or algorithm mimics cognitive functions that humans associate with other human minds. In particular, by training based on training data the trained function is able to adapt to new circumstances and to detect and extrapolate patterns.

In general, parameters of a trained function or algorithm can be adapted by way of training. In particular, supervised training, semi-supervised training, unsupervised training, reinforcement learning and/or active learning can be used. Furthermore, representation learning (an alternative term is "feature learning") can be used. In particular, the parameters of the trained functions can be adapted iteratively by several steps of training.

In particular, a trained function can comprise a neural network, a support vector machine, a decision tree and/or a Bayesian network, and/or the trained function can be based on k-means clustering, Q-learning, genetic algorithms and/or association rules. In particular, a neural network can be a deep neural network, a convolutional neural network or a convolutional deep neural network. Furthermore, a neural network can be an adversarial network, a deep adversarial network and/or a generative adversarial network.

The local algorithm and the algorithm dataset should not allow for the recovery of the local training data. This is typically true when the amount of data in the local training dataset is sufficiently large compared to the number of parameters in the algorithm dataset. It is especially true for training neural networks and most types of decision trees. For a few rare cases, e.g. the k-nearest neighbours algorithm, some part of the training data might be recovered. It is preferable to avoid the use of such algorithms for the local training.

The local system does not necessarily need to consist of a single computer or unit, e.g. a work station or a control unit in a medical imaging device. It is also possible that the local system can comprise one or multiple servers and even use a distributed data storage, even at remote locations. The local system can typically be assigned to a certain location and/or group of users. It can e.g. be the data processing system of a hospital or a group of hospitals.

The aggregating system can e.g. be operated by a manufacturer of medical devices or a provider of algorithms trained by machine learning. It can be a local system, e.g. a work station, a server, a set of multiple servers, implemented in a cloud, etc.

At least part of the local training data can be generated by applying an initial algorithm to local input data to generate local output data, providing a local data representation that depends on the local output data to a user and storing a user feedback provided by the user or a user information determined from the user feedback as part of the local training data. The local training and therefore as a result the aggregate algorithm can therefore take user feedback to the initial algorithm into account. This is especially useful when the method is used as part of an iterative process, wherein the aggregate algorithm is then rolled out as a new initial algorithm and therefore continuously improved based on the user feedback.

The user feedback can be a simple rating of the quality of the output data or the data representation. E.g. the user can assign a grade or a number of stars, e.g. between one and five stars, to the result. This can be directly used for reinforcement learning. E.g. the local algorithm can be slightly varied and the result of the variation can be rated to implement a reinforcement learning.

It is however also possible to use such ratings to train each local algorithm to recognize and rate good and bad outputs and aggregate these local algorithms, e.g. by using a majority voting or an averaging of their outputs. A reinforcement learning of the aggregate algorithm can then be implemented by varying the aggregate algorithm and rating the respective output of each variation by the aggregated local algorithms to create feedback for the reinforcement learning.

Additionally or alternatively it is possible to acquire changes to the output data or the data representation by the user as user feedback. E.g. a user might modify a segmentation that is output by the initial algorithm. This modified segmentation and the input data can then be used as input and output data during a supervised training of the local algorithm.

The training datasets can comprise additional data, e.g. the input data and/or the output data of the local algorithm and/or further data, e.g. patient data, data concerning the imaging conditions, etc. The input data can be locally acquired. The acquisition can be performed outside of the claimed method or in an additional step of the claimed method. The acquisition can be performed by a medical imaging device, e.g. by a computer tomograph or another device based on x-ray imaging, by a magnetic resonance tomograph or any other type of medical imaging device or sensors used during medical data acquisition. The local system can be the medical imaging device or a device used to acquire the medical data or a device to which that data is provided, e.g. a hospital database.

The aggregate algorithm can be updated in multiple iterations, wherein at least one of the iterations uses the aggregate algorithm determined during a previous iteration as the initial algorithm for the current iteration. This allows for a continuous improvement of the locally used algorithm. The respective initial algorithm used during a certain iteration can be an algorithm used to provide output data during the normal every day operation of e.g. a certain medical device. It can be updated at each iteration, especially when an updated aggregate algorithm is rolled out by the manufacturer of the device or another provider of the algorithm. During the normal operation, the collection of local training data and the training of the local algorithm can be performed and used to feedback the algorithm dataset that is then used to improve the initial algorithm in the next iteration.

The initial algorithm can be trained by machine learning using initial training data. If the aggregate algorithm is updated in multiple iterations as discussed above, it is especially possible that the initial algorithm during the first iteration is exclusively trained by initial training data that does not comprise any of the local training data and wherein the initial training is independent of any algorithm datasets generated during local training. In other words, the initial algorithm used during the first iteration or used before the aggregate algorithm is generated can be generated by a normal approach to machine learning, namely by using a sufficiently large, especially annotated and anonymized, dataset to perform an initial training. This initial training can then be improved by the discussed method of using a combination of local training and an aggregate algorithm.

At least part of the initial training data can be provided to the aggregating system and used to validate the aggregate algorithm and/or to determine a respective quality measure for each of the local algorithms, wherein the quality measures are used to generate the aggregate algorithm. Since the provider of the aggregate algorithm, e.g. a manufacturer of medical devices, has no or only limited control concerning the local training data and therefore the local training, it is advantageous to ensure that the aggregate algorithm does not show any unexpected behaviour and meets certain quality requirements. It can e.g. be tested if the aggregate algorithm performs at least as well as or at least within a certain margin of tolerance of the initial algorithm when applied to the initial training data or a certain selected part of the initial training data.

It is also possible to check the quality of the local algorithms before generating the aggregate algorithm, e.g. by applying the different local algorithms to at least part of the initial training data to determine the quality measure. It is then e.g. possible to only use some of the local algorithms selected depending on the respective quality measures to generate the aggregate algorithm or to e.g. use different weights when combining the different local algorithms into the aggregate algorithm. It is e.g. possible that the aggregate algorithm comprises multiple of the local algorithms, wherein the outputs of the local algorithms are averaged and/or a majority voting for the output is performed. In this case the quality measure can be used to determine a weight for the different local algorithms. E.g. a higher weight can be used when the local algorithm performs well on the initial training data or on a certain part of the initial training data.

At least part of the initial training data can be provided to each of the local systems and used to train the local algorithm. The local algorithm can therefore be trained using the local training data and at least part of the initial training data. This allows using a supervised local training even if the amount of available local training data is relatively small. It is e.g. possible to automatically install all or at least part of the initial training data on the local system when e.g. software for processing the medical data is installed or before a medical device is delivered to the customer. The installed part of the initial training data can then be combined with the local training data to provide a larger set of training data that can be used to train the local algorithm.

Instead of performing a completely new supervised learning for the local algorithm it is also possible to use approaches that can modify an initial algorithm based on new training data. An example of such an approach is e.g. to discuss already cited document US 2014/0219548 A1.

The user feedback can comprise a modification of the local data representation and/or the local output data and/or a rating concerning the quality of the local data representation and/or the local output data. Various uses for this kind of user feedback were already discussed previously.

The aggregate algorithm can comprise the evaluation of at least some of the local algorithms, wherein the outputs of the individual local algorithms are combined by a weighted or non-weighted averaging and/or majority voting. This was already discussed above. It is especially possible that the weighting can be determined based on the previously discussed quality measure.

It is also possible to generate an aggregate algorithm that does not comprise the evaluation of individual local algorithms. It is e.g. possible to use a user feedback that rates the quality of the local output data or the resulting local data representation, use pairs of input data and output data and the respective rating as training data to train an algorithm designed to rate the output data of the aggregate algorithm or a certain sub-algorithm of the aggregate algorithm and then use this algorithm to generate feedback during reinforcement learning of the aggregate algorithm. The discussed approaches to generating or training the aggregate algorithm are just some possible examples for this process. Any other approach that can generate an aggregate algorithm based a multitude of trained algorithms and/or algorithm datasets concerning these algorithms could be used.

The local algorithm and/or the aggregate algorithm and/or the initial algorithm can process image data as input data and output a segmentation of the image data and/or parameters concerning the anatomy of a patient depicted by the image data. Parameters concerning the anatomy can e.g. concern certain organs and/or vessels. It is also possible to detect and/or parametrize anomalies and/or to provide information about possible medical conditions. A possible output can e.g. be a segmented vessel or vessel tree, a tracing of a coronary, a relevant output of a CT-angio-application etc.

At least one embodiment of the invention also concerns an aggregate algorithm provided by the previously discussed method and a computer-readable storage medium containing information representing this algorithm. Information representing this algorithm can be a program or an instruction set implementing the trained algorithm or it can provide parameters determined during the training that parametrized a given algorithm comprising multiple free parameters, e.g. a neural network.

The described method can further be improved, when an incentive mechanism is used to motivate users of local systems to provide the algorithm dataset to a party providing the aggregate algorithm, e.g. a manufacturer of medical devices. It could e.g. be possible to offer updates of the aggregate algorithm only to users providing algorithm datasets or to provide such updates or updates of a program comprising the aggregate algorithm at a reduced price or for free for such users. Alternatively training courses, financial compensations etc. could be offered.

When user feedback is evaluated as part of the local training data this should typically be performed automatically. It might therefore be required that the feedback or any annotations of input data or output data need to confirm to certain technical requirements, e.g. be provided in a certain format. It is therefore advantageous, when the method comprises the step of providing recommendations about formatting or other technical requirements of the user feedback, e.g. annotations, to user prior to the submission of a current set of local training data.

While the quality of the individual local algorithms and/or the quality of the resulting aggregate algorithm can be validated as discussed above, it might still be advantageous to limit the local training to selected sites, user groups or individual users. If e.g. a segmentation algorithm should be improved by the method only a selected group of experts and their local systems could be used for local training.

At least one embodiment of the invention also concerns a method for processing medical data, especially medical image data, wherein the medical image data is processed by an aggregate algorithm that is generated by the inventive method discussed above to generate output data. The previously mentioned training is not a necessary part of the method for processing medical data, but the usage of the trained aggregate algorithm is part of this method.

Thus, in the most general terms, this embodiment of the invention provides a method for providing output data, namely processed medical image data. It can be a computer-implemented method and it e.g. comprises:

receiving input data, e.g. with a further first interface), applying a trained function/function trained by a machine learning algorithm (i.e. the aggregate algorithm) to the input data, e.g. with a computation unit, wherein the output data is generated, and providing the output data, e.g. with a further second interface.

It is especially advantageous when the method for processing medical data is simultaneously used to improve the aggregate algorithm by generating local training data or when a method for processing medical data using an initial algorithm is used to provide local training data, wherein the respective local training data can then be used to generate the aggregate algorithm as discussed above.

E.g. a local system can run an application for processing medical data that uses the initial algorithm or a first version of the aggregate algorithm to generate output data. The application can provide a user interface element by which the user can manually submit the current case to the local training data that can then be used to train the local algorithm as discussed above and therefore to generate or improve the aggregate algorithm. Alternatively this submission can be automatically performed for each case.

The user can e.g. rate the generated output data or data representation or provide other feedback, e.g. a modification of the results of the algorithm, e.g. a change to the segmentation. This user feedback can then be used as discussed above to train the local algorithm and therefore to generate the aggregate algorithm. Integrating the method for providing an aggregate algorithm closely with the method for processing medical data therefore allows users to actively participate in the improvement of the algorithms used for processing medical data with no or at least a minimal amount of additional effort. Due to the previously discussed method it can be ensured that it is not necessary to communicate any private data to the aggregating system that can e.g. be operated by the manufacturer of used medical device or some other service provider. The operator of the aggregating system can then e.g. validate the improved aggregate algorithm and then provide it as a free or paid update to the users. An updated algorithm can be rolled out as an update that only changes this algorithm or as part of an update to the application for processing medical data.

At least one embodiment of the invention also concerns a system comprising at least one processing unit configured to perform the function of the aggregating system in at least one embodiment of the inventive method for providing an aggregate algorithm and/or to perform at least one embodiment of the method for processing medical data. If the processing unit is configured to perform a method for processing medical data it can e.g. be integrated in a medical imaging device or be a work station used to evaluate the data from the medical imaging device. It is however also possible to perform this function e.g. by a server, a network comprising multiple servers or a cloud solution. The aggregating system will in many use cases require a relatively large amount of resources and can therefore e.g. be implemented on a server or a network of multiple servers or as a cloud solution. In some applications it can however also be advantageous to implement this functionality on a workstation or within a medical imaging system.

When the system comprises a processing unit configured to perform the function of the aggregating system it can additionally comprise multiple further processing units that are configured to perform the functions of the local systems in the method for providing an aggregate algorithm and/or to perform the method for processing medical data. In this case the system can especially be configured to implement the complete method for providing an aggregate algorithm. It is especially possible that the local systems are also used to process medical data as discussed above.

At least one embodiment of the invention further relates to a computer program that can be directly loaded into a memory unit of a processing unit, the computer program comprising instructions for performing the function of the aggregating system in the method for providing an aggregate algorithm and/or for performing at least one embodiment of the method for processing medical data when the program is executed on a processing unit.

At least one embodiment of the invention further relates to a computer-readable storage medium containing electronically readable instructions comprising the computer program.

In the following the solution according to at least one embodiment of the invention is described with respect to the claimed providing systems as well as with respect to the claimed methods. Features, advantages or alternative embodiments herein can be assigned to the other claimed objects and vice versa. In other words, claims for the providing systems can be improved with features described or claimed in the context of the methods. In this case, the functional features of the method are embodied by objective units of the providing system.

Furthermore, in the following the solution according to embodiments of the invention is described with respect to methods and systems for processing medical data processed by an aggregate algorithm as well as with respect to methods and systems for providing an aggregate algorithm for processing medical data. Features, advantages or alternative embodiments herein can be assigned to the other claimed objects and vice versa. In other words, claims for methods and systems for respective local algorithm can be improved with features described or claimed in context of the methods and systems for processing medical data processed by an aggregate algorithm, and vice versa.

In particular, the trained function or algorithm of the methods and systems for processing medical data processed by an aggregate algorithm can be adapted by the methods and systems for providing an aggregate algorithm for processing medical data.

FIG. 1 shows a schematic representation of a system 1 that can be used to provide an aggregate algorithm for processing medical data and to process medical data. The system 1 comprises multiple processing units 2-5. The processing units 2-4 implement a method for processing medical data, especially medical image data. An acquisition device 7, e.g. a medical imaging device, especially a computer tomograph or a magnetic resonance tomograph, is used to provide the medical data 6 to the respective processing units 2, 3, 4. In the example the acquisition device 7 is shown as a separate unit. It is however possible to integrate the processing units 2, 3, 4 as part of the respective acquisition device 7. The medical data 6 is processed by a program 8 to a generate output data 9 and a local data representation 10 that can e.g. be output on an output device 12, especially a monitor or a similar device, to inform the user about the output data 9. The program 8 can e.g. perform a segmentation of an image that is provided as medical data 6. Additionally or alternatively certain features in the medical data 6 can be classified etc. The program can be controlled by input device 13 by a user that can especially be used to record a feedback information 11.

The generation of the output data 9 as initially performed by using an initial algorithm 14 that can e.g. be preinstalled on the processing units 2, 3, 4. As described in more detail later this initial algorithm 14 can then be replaced by an aggregate algorithm 15 that can be updated at certain times.

Figure 2:
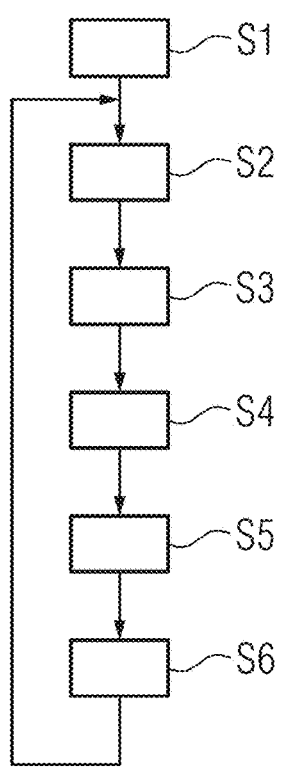

A method for providing such an aggregate algorithm 15 will now be discussed with additional reference to the flow chart shown in FIG. 2.

In step S1 an initial algorithm is provided. The initial algorithm can e.g. be provided by a manufacturer a medical imaging device or another device used for medical data acquisition. The initial algorithm can be trained by machine learning. This is discussed in more detail later with reference to FIG. 3.

In step S2 the initial algorithm or parameters describing the initial algorithm or a program comprising the initial algorithm is transferred to multiple local systems 16, 17, 18 that are implemented by the processing units 2, 3, 4 in the example shown in FIG. 1 and that can be used to process medical data 6 as discussed above. E.g. the initial algorithm 14 can be used to perform coronary tree segmentation.

During the processing of medical data 6 local training data 19 is generated in step S3 that does not leave the local system 16, 17, 18. To generate the local training data 19 the program 8 can e.g. provide at least one user interface element that allows the user to add the current case to the local training data. The user can be allowed to provide user feedback 11 with the input device 13 e.g. to rank the performance of the currently used algorithm and/or to modify the output data 9 or the data representation 10. The rating that can e.g. range from zero to five stars, wherein five stars can represent a complete satisfaction and zero or one star a strong dislike, and/or any modifications or the result of these modifications can be stored with the respective training dataset a part of the local training data 19.

At certain times or when a certain amount of local training data 19 is acquired training by machine learning 20 can be performed in step S4 to train a local algorithm 21 in the respective local system 16, 17, 18. For example a supervised learning can be implemented to teach the local algorithm 21 to generate output data 9 that already takes into account typical modifications of the output data or the local data representation by the user. Alternatively the local algorithm can be trained by reinforcement learning, e.g. using ratings provided as a user feedback. Alternatively or additionally ratings provided by the user can be used to trainer a local algorithm 21 that is able to predict a rating for a given output data and that can later be used for reinforcement learning for the aggregate algorithm.

Preferably the local algorithm 21 is not directly used in the local system 16, 17, 18, since it is not validated yet. Instead in step S5 a respective algorithm dataset 22 describing the respective local algorithm 21 is transferred from the respective local system 16, 17, 18 to an aggregating system 23 that is implemented by the processing unit 5 in the example shown in FIG. 1. The algorithm datasets 22 allow the aggregating system 23 to create local copies 24, 25, 26 of the local algorithms 21 generated in the local systems 16, 17, 18. The local algorithms 21 can therefore be used in step S6 to generate an aggregate algorithm 15 that aggregates the previous local learning. In a new version 8' of the program 8 the aggregate algorithm 15 can replace the initial algorithm 14 or a previous version of the aggregate algorithm.

After a validation of the aggregate algorithm 15 and/or the version 8' of the program 8 an update can be rolled out to the local systems 16, 17, 18.

The discussed method allows the ranked and potentially manually improved processing results to be fed back into the learning process, since the feedback 11 or a user information determined from this user feedback 11 is used to generate the local training data. The local training can involve but is not restricted to reinforcement learning, which updates models by awards or punishment based on the user rating, and/or methods that take into account newly arriving knowledge, e.g. in terms of the location of manual editing operations on geometric objects like vessel centrelines or organ segmentations. This way a knowledge pool is created consisting of medical image data and accompanying improved geometric objects that can be used for training at the customer side. While this information might comprise sensitive private data the inventive method avoids the transfer of this training data 19 itself by using a local training to generate a local algorithm and only use that algorithm or an algorithm dataset describing that algorithm in the further training process outside of the local system.

The locally improved or trained local algorithms 21 can then be transferred to an aggregating system, e.g. operated by a manufacturer of medical imaging equipment, at regular intervals or once a certain amount of local training data is collected. These algorithms are then used to generate the aggregate algorithm 15 that could also be labelled as supermodel. The local algorithms and therefore also the algorithm dataset typically merely represent a machine-readable representation of the acquired knowledge and cannot be deciphered by humans or by known algorithms to recover the used local training data. It can however still be advantageous to use authentication and/or encryption for the communication between the different local systems 16, 17, 18 and the aggregating system 23.

For the generation of the aggregate algorithm 15 ensemble learning techniques can be used. It is e.g. possible to implement the aggregate algorithm 15 in such a way that all or at least some of the local algorithms are executed and the output data can then e.g. be averaged or a majority voting can be used. It is possible to only use a selection of the local algorithms 21 or to use a different weighting for the outputs of different local algorithms 21. This will be discussed in more detail later with reference to FIG. 3.

The aggregate algorithm 15 can also be a higher-level algorithm consisting of a multitude of lower-level machine learning-based components. For example a coronary tracing could be implemented in such a way. The individual components can be subject to the discussed distributed approach wherein local algorithms 21 for the respective component are trained. The higher-level system can then be composed of multiple aggregate algorithms 15, each implementing a component of the more complex model.

Before the aggregate algorithm 15 is included in an updated version of a program 8' it can e.g. be validated. This will also be discussed in detail later. The updated aggregate algorithm 15 can be rolled out to be installed in the different local systems 16, 17, 18 as part of a service pack or a regular product release.

The use of aggregate algorithms that aggregate knowledge from a multitude of locally trained algorithms allows for the use of a bigger base of data than would be otherwise possible. This can improve a performance of machine learning-based systems. The resulting aggregate algorithm is especially expected to be superior to the individual local algorithms.

Figure 3:
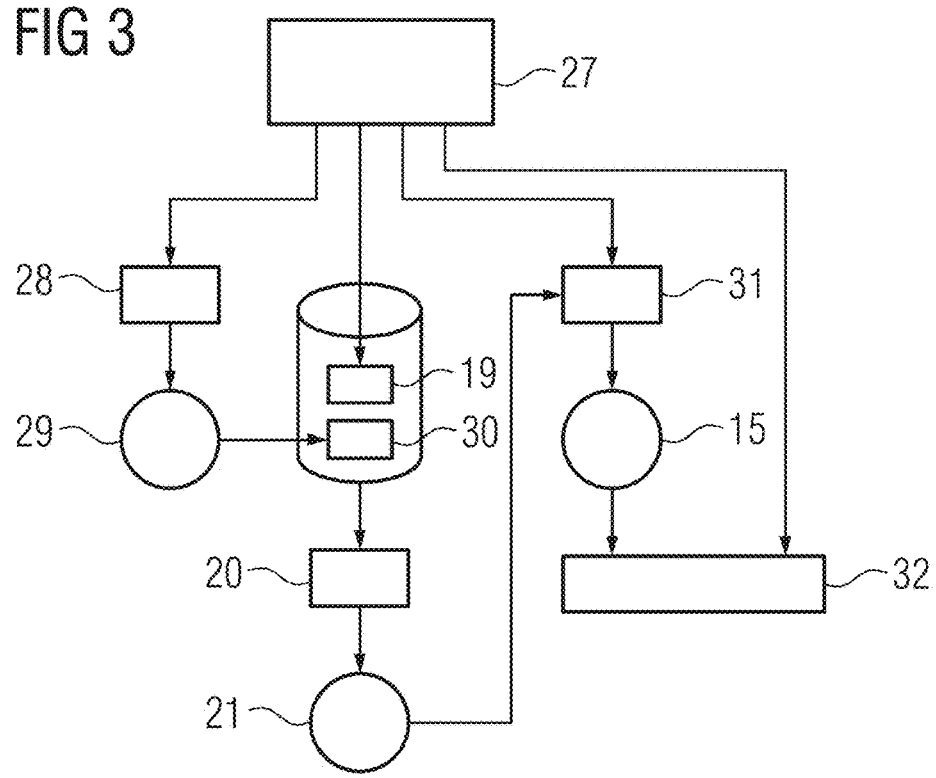

FIG. 3 schematically shows the use of initial training data 27 in the generation of an initial algorithm 29, the local algorithms 21 and the aggregate algorithm 15. The initial algorithm 29 can be trained by machine learning 28, using a well-known supervised learning approach that uses the initial training data 27. This is the usual approach of providing an algorithm trained by machine learning.

It is however possible to also use the initial training data 27 or at least a part 30 of an initial training data 27 in further steps during the generation of the aggregate algorithm 15.

It is for example possible to store at least a part 30 of the initial training data 27 on each of the local systems 16, 17, 18. This is especially advantageous when the local machine learning 20 is a supervised learning, since such a type of learning uses a multitude of training datasets. The storage of a part 30 of the initial training data 27 on the local systems 16, 17, 18 allows this machine learning 20 to be performed by using a large training database formed from the local training data 19 and at least a part 30 of the initial training data 27.

In the local systems 16, 17, 18 or in the aggregating system 23 a quality measure 31 that can be used as a weighting factor can be determined for each of the local algorithms 21 depending on at least part of the initial training data 27. It can especially be determined how well the individual local algorithms 21 perform when applied to input data from the initial training data 27. This information can be used to determine which of the local algorithms 21 should be used to generate the aggregate algorithm 15 and/or to determine weighting factors for the individual local algorithms 21 when they are combined to form the aggregate algorithm 15.

Once an aggregate algorithm 15 is determined a validation 32 can be performed, e.g. by applying the aggregate algorithm 15 on part of the initial training data 27. It is e.g. only possible to include the aggregate algorithm 15 in an update when its performance on the training dataset 27 is better or at least comparable to a previous version of the algorithm or the initial algorithm.

The proposed method offers an approach for the training of machine learning based classifiers or other machine learning based algorithms that are applied by end-users in the day-to-day routine. The users are able to contribute to the quality and performance of the used tool and will therefore directly benefit from their efforts when submitting, rating or amending data to generate the local training data. Since only data concerning the trained local algorithm is transferred to external systems, patient data does not need to leave the hospitals. Therefore there are no issues concerning data protection and no required separate anonymization step. The local algorithms and therefore the algorithm datasets do not carry any patient specific information.

Since the proposed method allows the use of user feedback to further train the algorithms there is no or at least less necessity of high quality annotations in the initial training data. The application of reinforcement learning techniques in combination with user ratings allows adding imperfect examples to the training, which will typically be based on the editing which is done by the user anyway. Therefore less in-house annotation efforts are required to improve algorithms. In-house annotations and other initial training data can e.g. only be used to provide an initial algorithm and for validating data versions of the algorithm.

The method allows for a larger pool of training data than would otherwise be achievable. Therefore a broader coverage of variables can be achieved. Differences in the local population can be captured in a better way during training and potentially the entire installed base could contribute to the training procedure. At the same time the combination of the local algorithms into an aggregate algorithm allow for achieving a better algorithm performance than by using only individual local models. A local validation and verification of local algorithms is not required, since this can be performed on the aggregating system.

Although the present invention has been described in detail with reference to the preferred embodiment, the present invention is not limited by the disclosed examples from which the skilled person is able to derive other variations without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing an aggregate algorithm for processing medical data, the method comprising:
    training a plurality of local algorithms by machine learning by training each respective local algorithm, of the plurality of local algorithms, on a respective local system using respective local training data;
    transferring a plurality of algorithm datasets corresponding to the plurality of local algorithms, respectively, to an aggregating system, each algorithm dataset of the plurality of algorithm datasets including at least one of a complete algorithm of the respective local algorithm or parameters for parameterizing a basic algorithm to reconstruct the respective local algorithm; and
    generating the aggregate algorithm by combining outputs of the plurality of local algorithms by at least one of
    a weighted or non-weighted averaging, or
    majority voting.

2. The method of claim 1, further comprising:
    generating at least part of the local training data by applying an initial algorithm to local input data to generate local output data, providing a local data representation depending on the local output data to a user, and storing at least one of a user feedback provided by the user or a user information determined from the user feedback as the at least part of the local training data.

3. The method of claim 2, further comprising:

updating the aggregate algorithm in multiple iterations, wherein at least one iteration of the multiple iterations includes generating a current iteration of the multiple iterations by using the aggregate algorithm determined during a previous iteration, of the multiple iterations, as the initial algorithm for the current iteration.

4. The method of claim 3, further comprising:

training the initial algorithm by machine learning using initial training data.

5. The method of claim 3, further comprising:

providing at least part of initial training data to the aggregating system; and at least one of validating the aggregate algorithm using the at least part of the initial training data, or determining, based on the at least part of the initial training data, a respective quality measure for each local algorithm of the plurality of local algorithms and generating the aggregate algorithm based on the quality measures.

6. The method of claim 4, further comprising:

providing at least part of the initial training data to the aggregating system; and at least one of validating the aggregate algorithm using the at least part of the initial training data, or determining, based on the at least part of the initial training data, a respective quality measure for each local algorithm of the plurality of local algorithms and generating the aggregate algorithm based on the quality measures.

7. The method of claim 2, further comprising:

training the initial algorithm by machine learning using initial training data.

8. The method of claim 7, further comprising:

providing at least part of the initial training data to the aggregating system; and at least one of validating the aggregate algorithm using the at least part of the initial training data, or determining, based on the at least part of the initial training data, a respective quality measure for each local algorithm of the plurality of local algorithms and generating the aggregate algorithm based on the quality measures.

9. The method of claim 8, further comprising:

providing at least part of the initial training data to each of the local systems; and training the plurality of local algorithms using the at least part of the initial training data.

10. The method of claim 7, further comprising:

providing at least part of the initial training data to each of the local systems; and training the plurality of local algorithms based on the at least part of the initial training data.

11. The method of claim 2, wherein the user feedback includes at least one of a modification of at least one of the local data representation or the local output data; or a rating concerning a quality of at least one of the local data representation or the local output data.

12. The method of claim 1, wherein at least one of the local algorithm, the aggregate algorithm or an initial algorithm is configured to process image data as input data, and output at least one of a segmentation of the image data or parameters concerning anatomy of a patient depicted by the image data.

13. A method for processing medical data, comprising:

processing the medical data by an aggregate algorithm, generated by the method of claim 1, to generate output data.

14. A non-transitory computer program product storing a computer program, directly loadable into a memory of a processor, the computer program including instructions for performing the method of claim 10 when the program is executed by the processor.

15. A non-transitory computer-readable storage medium storing electronically readable instructions for performing the method of claim 10 when the electronically readable instructions are executed by a processor.

16. A non-transitory computer program product storing a computer program, directly loadable into a memory of a processor, the computer program including instructions for performing the method of claim 1 when the program is executed by the processor.

17. A non-transitory computer-readable storage medium storing electronically readable instructions for performing the method of claim 1 when the electronically readable instructions are executed by a processor.

18. The method of claim 1, wherein the medical data is medical image data.

19. A system comprising:

at least one processor configured to cause the system to train a plurality of local algorithms by machine learning by training each respective local algorithm, of the plurality of local algorithms, on a respective local system using respective local training data;

transfer a plurality of algorithm datasets corresponding to the plurality of local algorithms, respectively, to an aggregating system, each algorithm dataset of the plurality of algorithm datasets including at least one of a complete algorithm of the respective local algorithm or parameters for parameterizing a basic algorithm to reconstruct the respective local algorithm; and generate the aggregate algorithm by combining outputs of the plurality of local algorithms by at least one of a weighted or non-weighted averaging, or majority voting.

20. The system of claim 19, wherein the at least one processor comprises multiple further processors, each configured to perform a function of a local system.

21. The system of claim 19, wherein the at least one processor is further configured to cause the system to:

generate output data by processing data by the aggregate algorithm.

* * * * *